(12) United States Patent
Ruchala et al.

(10) Patent No.: US 10,939,891 B2
(45) Date of Patent: Mar. 9, 2021

(54) AUTOMATED DETECTION AND IDENTIFICATION OF PHANTOMS

(71) Applicant: Gammex, Inc., Middleton, WI (US)

(72) Inventors: Kenneth Ruchala, Madison, WI (US); Eric Schloesser, Mt. Horeb, WI (US); Thomas Kammeyer, Madison, WI (US); Jason Holzmann, Middleton, WI (US); Cristel Baiu, Madison, WI (US); Mark Holmes, Middleton, WI (US)

(73) Assignee: Gammex, Inc., Middleton, WI (US)

(*) Notice: Subject to any disclaimer, the term of this patent is extended or adjusted under 35 U.S.C. 154(b) by 458 days.

(21) Appl. No.: 15/821,297

(22) Filed: Nov. 22, 2017

(65) Prior Publication Data
US 2018/0140272 A1   May 24, 2018

Related U.S. Application Data (60) Provisional application No. 62/425,690, filed on Nov. 23, 2016.

(51) Int. Cl.
| | | |
|---|---|---|
| *A61B 6/00* | (2006.01) | |
| *A61B 6/03* | (2006.01) | |
| *G01T 1/161* | (2006.01) | |
| *G01T 7/00* | (2006.01) | |
| *A61N 5/10* | (2006.01) | |

(52) U.S. Cl.
CPC ............ *A61B 6/583* (2013.01); *A61B 6/032* (2013.01); *A61B 6/4435* (2013.01); *A61B 6/545* (2013.01); *A61N 5/1075* (2013.01); *G01T 1/161* (2013.01); *G01T 7/005* (2013.01); *A61N 2005/1076* (2013.01)

(58) Field of Classification Search
None
See application file for complete search history.

(56) References Cited

U.S. PATENT DOCUMENTS

| | | |
|---|---|---|
| 4,788,706 A | 11/1988 | Jacobson |
| 7,510,325 B2 | 3/2009 | Endo et al. |
| 9,198,633 B2 | 12/2015 | Freeman et al. |

(Continued)

FOREIGN PATENT DOCUMENTS

| | | |
|---|---|---|
| WO | 2016137425 A1 | 9/2016 |
| WO | 2016138449 A1 | 9/2016 |
| WO | 2016181182 A1 | 11/2016 |

OTHER PUBLICATIONS

Multi-Energy CT Phantom Model 1472 Manual by Gammex, Inc., 2016.

(Continued)

*Primary Examiner* — Hoon K Song
(74) *Attorney, Agent, or Firm* — Andrus Intellectual Property Law, LLP (57) ABSTRACT

A phantom, phantom system, and method of phantom identification include a first material that forms a phantom. A phantom identifier includes at least one unit marker. The at least one unit marker identifies a physical characteristic of the phantom. In a method of phantom identification, an image of the phantom is obtained that includes the phantom identifier. The at least one unit marker is identified, the at least one unit marker encodes a value representative of a physical characteristic of the phantom.

17 Claims, 7 Drawing Sheets

(56) References Cited

U.S. PATENT DOCUMENTS

| | | | |
|---|---|---|---|
| 2012/0076371 A1* | 3/2012 | Caruba | A61B 6/4417 382/128 |
| 2015/0030223 A1* | 1/2015 | Pearlstein | G06T 5/20 382/131 |
| 2016/0015356 A1* | 1/2016 | Baiu | A61B 6/583 378/207 |

OTHER PUBLICATIONS

Tissue Characterization Phantom Model 467 Manual by Gammex, Inc., 2016.
International Search Report and Written Opinion for PCT/US2017/063083 dated Feb. 27, 2018.

* cited by examiner

AUTOMATED DETECTION AND IDENTIFICATION OF PHANTOMS

CROSS-REFERENCE TO RELATED APPLICATION

The present application claims priority of U.S. Provisional Patent Application No. 62/425,690, filed on Nov. 23, 2016, the content of which is hereby incorporated herein by reference in its entirety.

BACKGROUND

The present disclosure is related to the configuration and calibration of radiographic and/or radiotherapeutic devices using a phantom. More specifically, the present disclosure relates to phantoms that may be automatedly detected and identified by a calibration system.

Objects of materials that represent a quantity of one or more body structures or known values for reference in calibration purposes are generally known as phantoms. Phantoms represent one or more characteristics or properties (e.g. mass, composition, dimension, shape, magnetic moment, or attenuation). Such phantoms are used in the medical field for quality control and quality assurance of medical imaging and radiotherapy devices. Quality assurance testing can be a part of initial setup and calibration of an imaging or radiotherapy device, or can be used as part of a routine quality assurance program to maintain optimal system performance. The American College of Radiology (ACR) offers a volunteer program of CT device quality assurance that includes the use of phantoms for CT device accreditation.

In fields such as medical imaging and radiotherapy, there are numerous quality assurance protocols. It is common during these protocols to scan/radiate/analyze one or more phantoms and evaluate the collected data using the appropriate protocols for the desired calibration or quality assurance purpose. Often, protocols require a particular or specialized combination of phantoms that must be scanned during the protocol. Phantoms can be constructed as immutable objects with a fixed combination of phantom materials at known locations. Alternatively, a phantom may include a plurality of interchangeable inserts and as such may be configured and reconfigured to provide the user with more testing options. Phantoms may also be constructed modularly, such as through a series of slabs, in which the individual modules are immutable but the arrangement might vary based on the user and/or protocol. Immutable phantoms have a downside of limiting testing options, while reconfigurable phantoms are time consuming to configure and each material insert must be manually registered into the system before the analysis may be conducted.

In a current workflow using a reconfigurable phantom, a plurality of material inserts are arranged in a phantom base. The phantom base with the inserts in place is positioned within the CT machine and imaged. A technician commonly photographs the material inserts positioned in the phantom base or otherwise manually records the arrangement of inserts in the phantom base. The technician enters this information into the computer. The technician views at least one CT image taken of the phantom and manually specifies which phantom base was imaged. The technician further, with reference to the photograph and/or manual record of the insert arrangement, specifies the location and material of each insert to the computer system. The computer system is then able to run the analysis of the desired protocol. This creates a workflow setting wherein a significant amount of technician time is used prior to running a protocol analysis. The above described workflow is further subject to error as a technician may make a mistake when identifying an insert or in specifying the identity of an insert to the computer system. The above workflow further requires additional record keeping. Since the workflow requires the collection and analysis of additional records, these records must be maintained and stored for future analysis or QA auditing.

Therefore, phantom solutions that can enable more efficient protocol workflows and increase flexibility and automation of calibration and/or quality assurance protocols are desired.

BRIEF DISCLOSURE

In an exemplary embodiment of a phantom for use in calibration of a medical device, the phantom includes a first material that forms the phantom. A phantom identifier includes at least one unit marker. The at least one unit marker identifies a physical characteristic of the phantom.

In a further exemplary embodiment, the phantom identifier further includes at least one reference marker and the at least one reference marker is indicative of an orientation of the phantom identifier. In a still further exemplary embodiment, the at least one unit marker encodes an identification of the first material in a positional grid representative of binary unit values.

A phantom system for use in calibration of a medical device includes a phantom base. The phantom base includes at least a first material. A first phantom component is positioned within the phantom base. The first phantom component includes a second material. A first phantom component identifier is connected to the first phantom component. The first phantom component identifier includes at least one first phantom component unit marker. The at least one first phantom component unit marker encodes an identification of the second material. A second phantom component is positioned within the phantom base. The second phantom component includes a third material. A second phantom component identifier is connected to the second phantom component. The second phantom component identifier includes at least one second phantom component unit marker. The at least one second phantom component unit marker encodes an identification of the third material.

In a further exemplary embodiment of a phantom system, the first phantom component identifier includes at least one first phantom component reference marker and the second phantom component identifier includes at least one second phantom component reference marker. The at least one first phantom component reference marker is indicative of an orientation of the first phantom component identifier. The at least one second phantom component reference marker is indicative of an orientation of the second phantom component identifier.

A method of phantom identification includes obtaining an image of a phantom that includes a phantom identifier that includes at least one unit marker. At least one unit marker is identified in the image of the phantom. A value, encoded by the at least one unit marker, is decoded. The phantom is identified based upon the decoded value.

In a further exemplary embodiment of a method of phantom identification, the phantom identifier includes at least one reference marker. The at least one reference marker is identified in the image of the phantom. The image orientation is determined from the identified at least one reference marker.

DETAILED DISCLOSURE

Medical imaging applications seek to provide visual representations of bodily structures, organs, and organ systems. Computed tomography (CT) is one known platform for diagnostic imaging. While CT will exemplarily be used throughout the current description, it will be understood by one of ordinary skill in the art that embodiments as disclosed herein may be used with other modalities of imaging devices used in the medical field. In such other exemplary embodiments, rod identifiers as described herein are selected to produce contrast in the modality used. Still other exemplary embodiments as disclosed herein may be used in connection with radiotherapy systems/devices.

Figure 1:
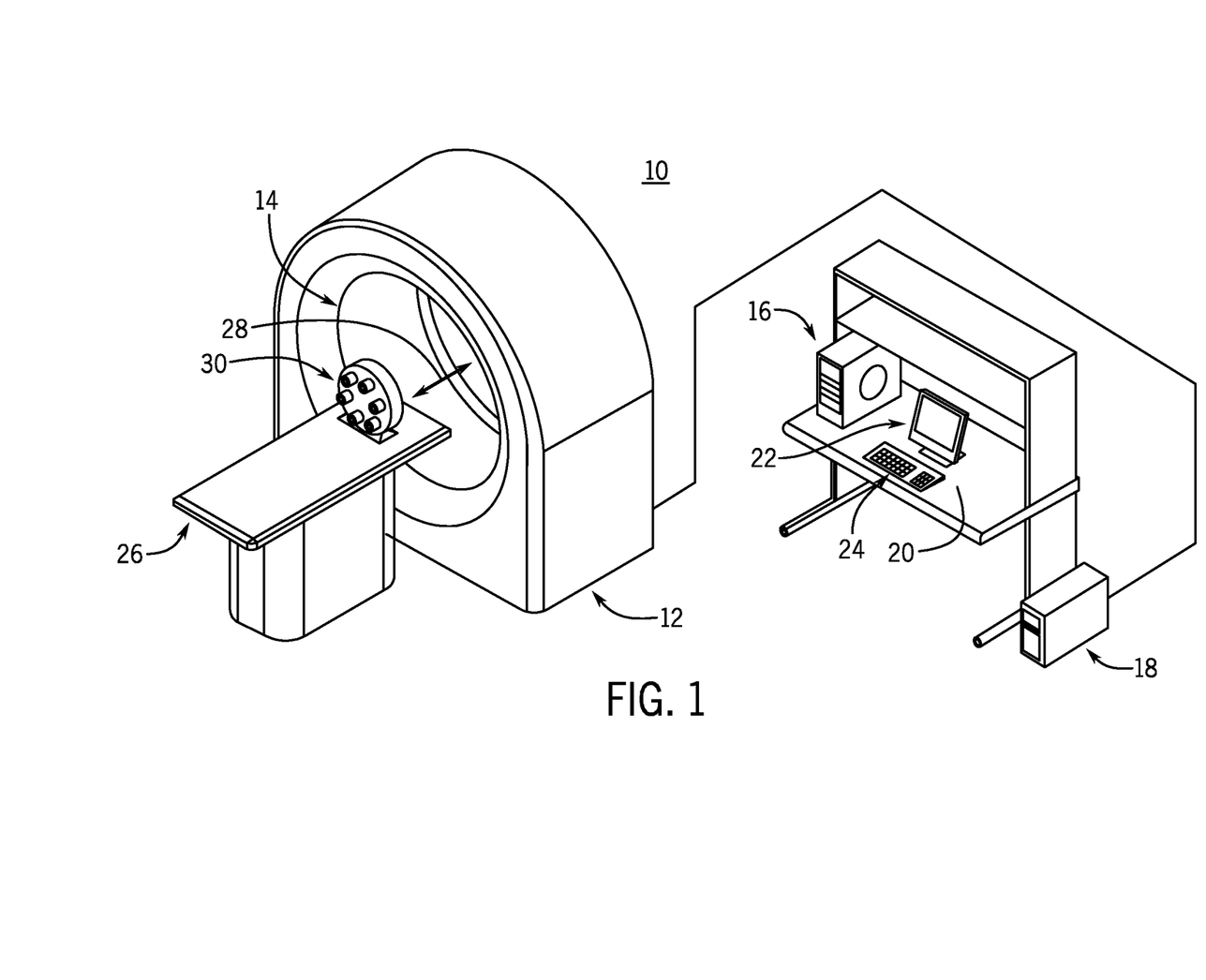
FIG. 1 is a system diagram depicting an exemplary embodiment of a phantom in use with a CT device.

FIG. 1 depicts a medical imaging system 10. The medical imaging system 10 includes a computed tomography (CT) device 12. The CT device 12 includes one or more x-ray radiation sources (not depicted) that rotate about a defined path. The radiation sources are supported by a circular gantry 14 or a C-arm (not depicted). It will be recognized that some embodiments of the CT device 12 may be single energy (SE), dual energy (DE), or multiple energy (ME), which references the number of energy levels used during a single imaging session.

The CT device 12 is communicatively connected to a computer 16 or another processing unit. In one embodiment, the computer 16 is integrated with the CT device 12 and in an alternative embodiment, the computer 16 is a separate component that is communicatively connected such as with wired or wireless communication platforms. The computer 16 executes computer readable code that is either stored locally or at a remote computer storage location, such as a server 18 that is communicatively connected to the computer 16 by wired or wireless communication networks.

The computer 16 executes the computer readable code to operate the CT device 12 in order to capture medical images in the manner directed by a clinician or other user through a user interface 20. The user interface 20 comprises a graphical display 22 that presents one or more graphical user interfaces (GUI) that present captured medical images or user input prompts, other medical or patient information, or a combination thereof. The user input device 20 further includes a data entry device 24 that is exemplarily a keyboard, mouse, or touch screen, or any other of a variety of data entry devices as would be recognized by one of ordinary skill in the art. In alternative embodiments, the computer 16, user interface 20, graphical display 22, and data entry device 24 can be integrated into any of a variety of devices, such as, but not limited to, desktop computers, laptop computers, tablet computers, or mobile computers/smartphones.

The medical imaging system 10 further includes a movable patient support 26. The movable patient support 26 is configured to support a patient or other subject for imaging by the CT device 12. The movable patient support 26 translates along arrow 28 to position the subject within the gantry 14. Additionally, the movable patient support 26 can be movable along additional axes, including but not limited to four degrees of freedom movement. The positioning of the subject within the gantry 14 on the patient support 26 aligns a particular region of interest (ROI) of the subject with an imaging plane of the one or more radiation sources of the CT device 12. The one or more radiation sources of the CT device 12 each produce image slices through the subject along the imaging plane. The translation of the movable patient support 26 changes the ROI of the patient that is imaged by the CT device. An exemplary embodiment of a phantom 30 as described in further detail herein is depicted as being placed on the movable patient support 26. The phantom 30 is comprised of at least one material that mimics an anatomical structure, material, or physical property relevant to the radiographic or radiotherapeutic application.

While the present disclose uses examples of specific phantom structures and/or arrangements, it is to be recognized that any of a variety of known or yet to be developed phantoms may incorporate features as disclosed herein while remaining within the scope of the present disclosure. Phantoms known besides those non-limiting examples as described herein, may be modified to include features as disclosed to identify a phantom as a whole, or individual components of phantoms with interchangeable or reconfigurable components. In embodiments, the individual phantom components may be rods, as used for exemplary purposes herein, but may also be modular sections of other shapes or configurations, and which may be arranged with more or fewer components and in different arrangement orders of components. In further embodiments, the phantom components may exemplarily be slabs, plates, or discs of phantom material. Embodiments as disclosed herein can be used to identify the phantom components and the order of the phantom components within the phantom as a whole.

Figure 2:
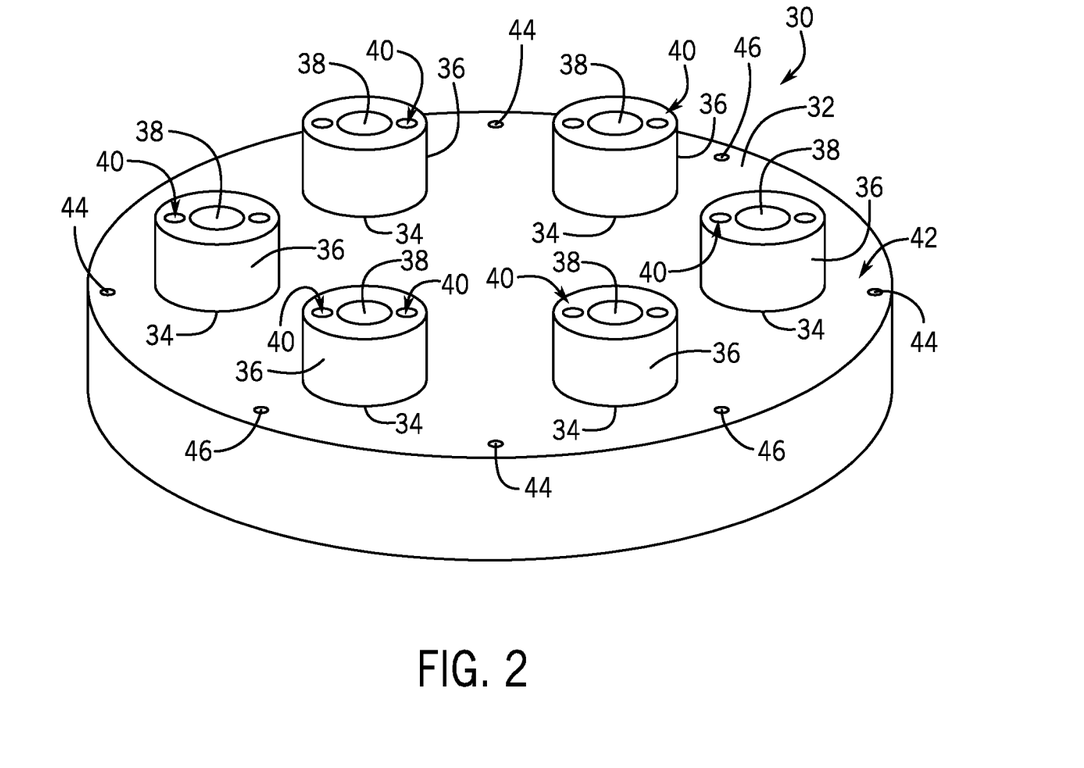
FIG. 2 depicts an exemplary embodiment of a phantom.

FIG. 2 depicts an exemplary embodiment of a phantom 30 as disclosed herein. The phantom 30 includes a phantom base 32 that is exemplarily constructed of a material with known physical properties, particularly known physical properties relevant to the calibration procedures used and described herein. In an example, the phantom 30 is constructed of a material with an electron density that mimics water. As a non-limiting example, the base 32 may be exemplarily constructed of SOLID WATER® water equivalent material available from Gammex, Inc. In an embodiment, the SOLID WATER® water equivalent material is used as a neutral reference relative to the materials of other phantoms used as described herein with the phantom base 32. In other exemplary embodiments, the material or composition of the phantom base 32 may not be specifically known to the medical imaging system 10, and rather an identification of one or more physical properties of the phantom base 32 encoded in the phantom base 32 in the manners as described in further detail herein. The phantom base 32 includes a plurality of holes 34, exemplarily arranged in a predetermined pattern. It will be recognized that various hole arrangements may be used in different phantoms 30 and may represent phantom bases 32 configured to be used in various/or particular procedures.

In the exemplary embodiment depicted, removable phantom components in the form of a plurality of phantom rods 36 are inserted into the holes 34. The phantom rods 36 are constructed of specific materials that are designed to mimic one or more physical characteristics or properties of a body tissue or tissues as will be described herein, or to provide a specific reference value for one or more of these characteristics. In non-limiting examples, these physical characteristics may include specific densities, electron densities, magnetic moments, shapes, positional relationships, elemental compositions, attenuation, or mass.

While the phantom 30 is depicted in FIG. 2 as a phantom 30 having interchangeable rods 36 inserted into any of the plurality of holes 34, it will be recognized that other examples of phantoms as may be used in embodiments as disclosed herein may have the rods be in fixed positions relative to the base and/or constructed as a unitary device without interchangeability. In still further exemplary embodiments the phantom components may take a form other than rods and may be moveably fixed to the phantom base, thus while their relative positions may be changed, the phantom itself contains a predetermined and fixed set of phantom components. A modular phantom consisting of phantom components of different slabs or sections that could be re-arranged would be such an embodiment. Similarly, a modular phantom might have the ability to add, change, or decrease the number of modular phantom components used.

Referring back to FIG. 2, in exemplary embodiments, the insertable rods 36 include visible label 38, which is exemplarily affixed to one end of the rod 36, typically the end of the rods opposite the end that is inserted into the hole 34 in the base 32. The visible label 38 may include color, alphanumeric, and/or textual indications regarding the material and/or structure of the rod 36. While the labels 38 visibly identify the material of the rod 36 to a technician, these labels are not visible or otherwise readable by a radiotherapy device or a medical imaging device (e.g. CT). Therefore, as described in further detail herein, each of the rods 36 are provided with rod identifiers 40 which are constructed in the manners as described herein to provide a machine detectable identification of each of the rods 36. In still further embodiments, the phantom 30 includes phantom identifiers 42, for example in the phantom base 32. In an embodiment wherein the rods 36 are interchangeable with the base 32, the phantom identifiers 42 identify the particular phantom base 32. In embodiments wherein the phantom 30 is a fixed construction of a phantom base 32 and one or more phantom components, the phantom identifiers 42 may identify the entire phantom 30 itself. In modular embodiments, the phantom identifiers 42 may identify the presence, order, and/or orientation of each modular phantom component being used.

Figure 3A:
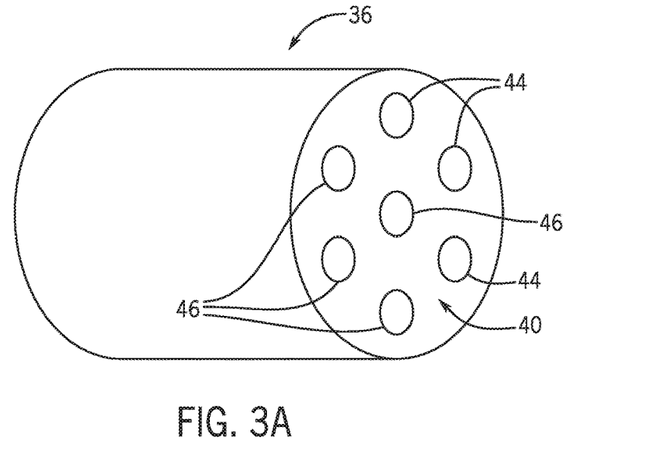
FIG. 3A is a perspective view of an exemplary embodiment of an insertable rod.

FIG. 3A is a perspective view of an exemplary embodiment of a phantom component in the form of an insertable rod 36. The rod 36 includes a rod identifier 40, which exemplarily is a plurality of holes, or as exemplarily provided herein may be any of a variety of markers that represent identifiable properties as may exist in medical imaging or radiotherapy procedures. Nonlimiting examples in addition to holes that may be used as the individual markers in the identifier 40 are inserts of metal, plastic, or other material, which may be in the form of cylinders, BBs, beads, or other identifiable shapes. It will be recognized that in embodiments, a degree of contrast between the material of the individual markers and the material of the rod 36 is desirable. This degree of contrast may further be with consideration of the imaging modality being used. Nonlimiting examples of identifiable contrast as may be detected to identify the markers of the identifier relative to the phantom base include density, electron density, magnetic moment, elemental composition, attenuation, or mass. In one such exemplary embodiment, holes or voids provide an advantageous embodiment as the air in such voids will differ from the material of the rod 36 in numerous characteristics or values, one or more of which may be relied upon during a procedure to detect the markers of the identifier 40. For example, air differs substantially from most materials in the properties of mass, electron density, and magnetic movement. Additionally, air is less prone to cause artifacts in CT compared to adding high-density materials.

In an exemplary embodiment, the identifier 40 exemplarily includes orientation markers 44 and unit markers 46. In exemplary embodiments which will be described in greater detail herein, the orientation markers 44 combine to provide an indication of the rotation, inversion, and/or scale of the rod 36 when imaged. The unit marker 46 combined to uniquely identify the specific rod out of a plurality of known or predefined rods.

Figure 3B:
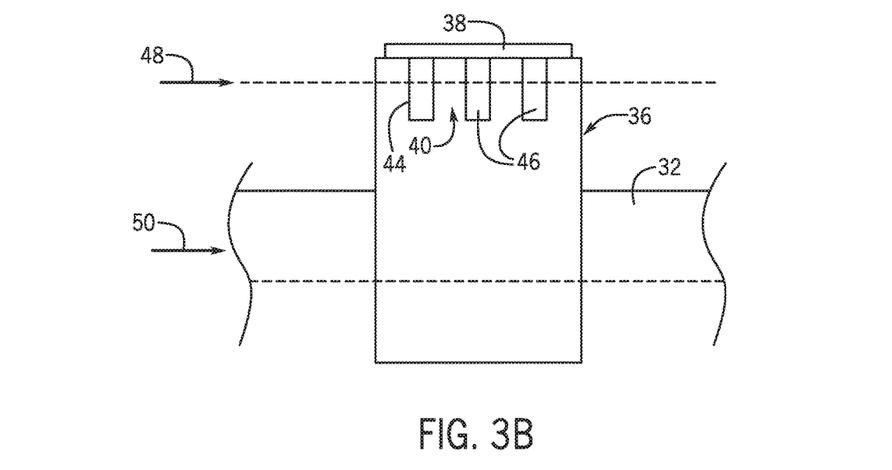
FIG. 3B is a sectional view of an exemplary embodiment of an insertable rod.
Figure 3C:
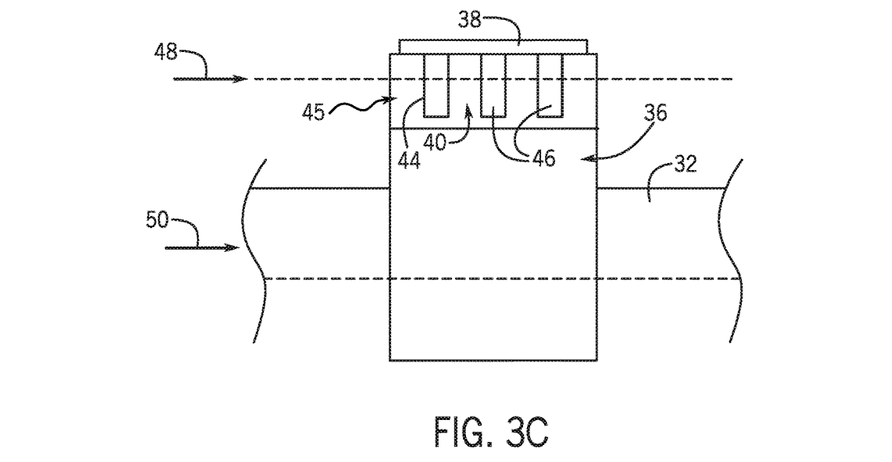
FIG. 3C is a sectional view of a further example of an insertable rod.

FIG. 3B is a sectional view of an exemplary embodiment of an insertable rod 36. In the exemplary sectional view of the rod 36, it can be seen that the rod identifiers 40 are located at one end of the rod 36. In an exemplary embodiment, this may be the end of the rod 36 that extends out from the phantom base 32. In such an exemplary embodiment, the rod identifiers 40, which may include both the orientation marker 44 and the unit markers 46, may be positioned below the label 38, such that the rod identifiers 40 are not visible. In a still further exemplary embodiment, wherein the rod identifiers 40 are voids 34, for example holes extending from one end. Positioning of the rod identifiers 40 below the label 38 may exemplarily protect the voids 34 from debris or other material which may interfere with their identification and detection. In still further embodiments, the rod identifiers 40 may still be voids, but may be located internal from the end of the rod 36, such that the voids are not visible or otherwise accessible. In a still further example as shown in FIG. 3C, the voids 34 or other rod identifiers 40 may be provided within an endcap 45 of a material different from the material of the rest of the rod 36, the material of the end cap 45 selected to promote detection and identification of the rod identifiers 40 in clinical imaging and/or radiotherapy procedures.

While the rod identifiers 40 are exemplarily depicted as being located in the end of the rod 36 that extends out of the base 32, it will be recognized that the rod identifiers 40 may alternatively be located in the end of the rod 36 inserted into the base 32, or may be located at another location or position within the rod 36.

In an exemplary embodiment, the location of the rod identifiers 40 within the rod 36 are known such that an identification scan plane, for example as represented by arrow 48, is imaged in order to image the rod identifier 40 for identification of the rod 36. The identification scan plane 48 is exemplarily different from one or more analysis scan plane(s) as exemplarily represented by arrow 50. In an exemplary embodiment, the identification scan plane 48 is different from and apart from the procedure scan plane 50 such that the rod identifiers 40 do not interfere with or in any way affect or impinge upon the scans used for the procedure, exemplarily calibration or quality assurance procedures.

FIGS. 4A-E depict exemplary embodiments of patterns that may be used in the rod identifiers as described herein.

Figure 4A:
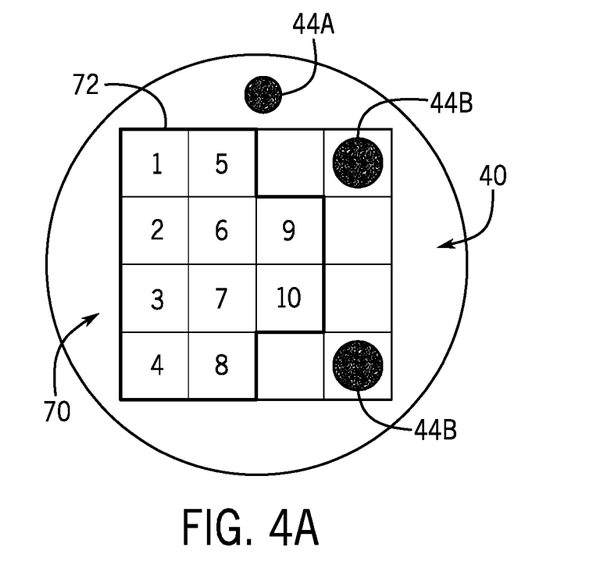
FIGS. 4A-4E depict exemplary embodiments of rod identifiers.

FIG. 4A depicts an exemplary embodiment of an arrangement which may be used to provide rod identifiers 40. It is understood that in exemplary embodiments of rod identifiers, the encoding system used by the rod identifier is able to encode a large number of unique identities. For example, in one embodiment, the rod identifier encodes ten bits of information for identity encoding while in another embodiment, the rod identifier may encode more information, including, but not limited to twelve bits or more of information. In one embodiment as disclosed herein, the rod identifier exemplarily is able to encode 1,000 or more different identifications, for example as encoded in ten bits or more of information. In the exemplary embodiment depicted, the rod identifier is exemplarily spatially arranged in a grid 70. The gird 70 is exemplarily a 4×4 grid. While the grid 70 is graphically shown in FIGS. 4A-4E, it will be recognized that this may be for descriptive purposes and that in use no observable grid may be present. The markers as described herein may still be arranged within the grid 70 as described without a physical or visible grid being present. In an exemplary embodiment, the grid 70 may be a 4×4 grid as depicted and the squares of the gird 70 may be 4 mm by 4 mm, although it will be recognized that any number of squares and square sizes may be used in embodiments of the grid 70.

An additional reference marker 44A outside of the grid which indicates the "top" or a reference orientation of the identifier 40. Reference markers 44B are located within the 4×4 grid, but are additionally distinguishable from other markers either by size, shape, or other means of identification. As previously noted, the grid may exemplarily be comprised of 4 mm by 4 mm squares. Within this example reference marker 44B may be distinguishable from reference marker 44A and the unit markers 46 based upon size. The reference markers 44B are exemplarily 3 mm in diameter while the reference marker 44A and the unit markers 46 are 2 mm in diameter. Reference markers 44B and unit markers are exemplarily positioned centered within a respective square of the grid 70 so that center-to-center distances of the unit markers within adjacent squares are consistent and identifiable.

The reference markers 44A and 44B combine to reliably identify the rotation, inversion, and scale of the image. The rotation of the image of the identifier 40 is determined using reference markers 44A which indicates the "top" or reference position of the grid 70. Inversion of an image of the identifier 40 can be determined from the position of the reference markers 44B, which have a known relation to the reference markers 44A. In the example shown, the reference markers 44B are positioned to the right of the reference markers 44A when in the correct orientation. Reference markers 44B appearing to the left of the reference markers 44A would indicate that the image is inverted. Scale of the image of the identifier can be determined based upon known sizes of the markers as a reference. In the example given, the reference marker 44A and the unit markers are 2 mm in diameter, the reference markers 44B are 3 mm in diameter and adjacent markers within the grid are 4 mm center-to-center. Comparison of the image to these known reference identify the scale of the image.

Once the image is verified, the positions can be identified and the system can determine the rest of the grid in which the identification of the rod is encoded. In exemplary embodiments, the reference markers 44, alone or in combination with the unit markers 46 uniquely present the rod identifier 40 independent from phantom or rod orientation and phantom or rod inversion, and do so without aliasing, meaning that no two patterns of the rod identifier 40 when combined with different orientations or inversion would be mistaken for one another.

In a merely exemplary embodiment, the identification of the rod is encoded in the positions of the grid 70 as identified in FIG. 4A. In the exemplary arrangement, unit markers 46 as explained in further detail herein at the depicted positions within the grid 70 encode ten bits of information exemplarily used to specify the particular rod. These ten bits are diagrammatically bound by a reference border 72 in FIG. 4A. In a non-limiting embodiment, unit marker positions 1-8 are used to identify the rod material with 8 bits of information (e.g. 256 combinations) while unit marker locations 9 and 10 are used to indicate the version of the rod and/or material with 2 bits (e.g. 4 combinations). As noted above, in an exemplary embodiment, the reference marker 44 and the unit markers 46 as described herein are 2 mm in diameter and the reference markers 44B are exemplarily 3 mm in diameter. In an exemplary embodiment, the grid spaces immediately adjacent the reference markers 44B may be left open to ensure greater spacing from these larger diameter reference markers 44B from any of the unit markers 46. In the exemplary and non-limiting embodiment described herein, all of the reference markers are holes 1 cm deep. In the embodiment depicted, the rod identifiers 40 are all contained within a 1 inch circle as depicted and thus can be positioned in either end of the rod as described above. In exemplary embodiments the rod identifiers 40 may be covered by a label 38 over an end of a rod. It will be recognized that these are merely exemplary measurements and are not intended in any way to be limiting on the scope of the disclosure provided herein and implementation of embodiments of the disclosure.

Figure 4B:
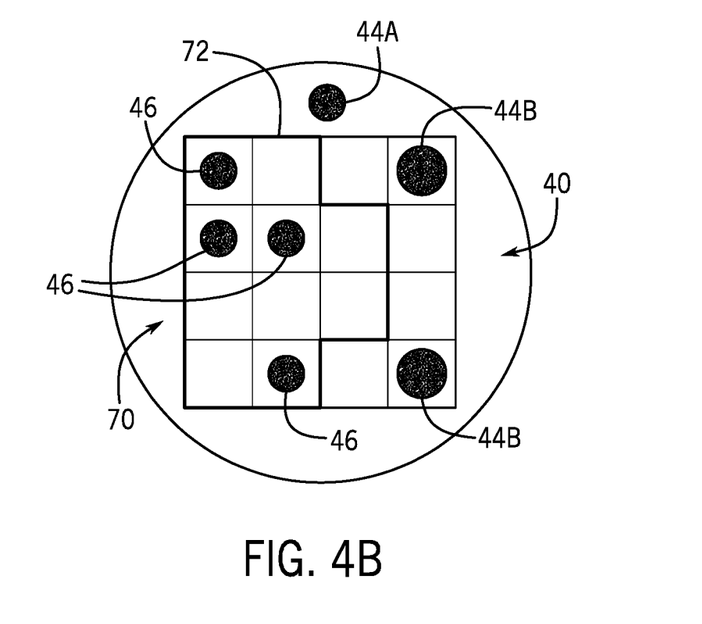

FIG. 4B depicts an exemplary embodiment of rod identifier 40 exemplarily encoding an identification of a rod material. In the embodiment depicted, the reference markers 44A and 44B define the rotation, inversion, and scale of the rod as imaged. The rotation of the rod is needed such that the unit marker 46 can be accurately interpreted within the grid additionally, the reference markers 44A, 44B are used to detect against inversion (e.g. wherein the phantom or the rod is rotated such that superior and inferior positions are reversed). As mentioned above, in embodiments, each of the patterns of the unit markers 46 are identifiable without aliasing and, for example, are provided with at least 2-3 mm of space between markers.

In an exemplary embodiment, each bit defined by the array is "on" (1) if a unit marker is located at that position and "off" (0) if no unit marker 46 is located there. Thus, in the example provided in FIG. 4B, there are unit markers 46 located at positions "1", "2", "6", and "8". Therefore, this arrangement of unit markers encodes the number 1+2+32+128=163. Upon a procedure system detecting this code number encoded with the rod identifiers, this code is used to look up a corresponding material or rod in a lookup table. An exemplary and nonlimiting embodiment of such a table with materials available from Gammex, Inc. is provided below:

TABLE 1

| Material | Product # | Code # | Bits "on" |
|---|---|---|---|
| 451 Solid Water | 451 | 1 | 1 |
| 457 Solid Water | 457 | 2 | 2 |
| 486 Solid Water | 486 | 3 | 1, 2 |
| 1451 Solid Water | 1451 | 4 | 3 |
| 1557 Solid Water | 1557 | 5 | 1, 3 |
| Brain | | 32 | 6 |
| Brain HE | 1481 | 33 | 1, 6 |
| Breast | | 36 | 3, 6 |
| Liver (LV1) | | 40 | 4, 6 |
| Adipose (AP6) | | 44 | 3, 4, 6 |
| General Adipose HE | 1553 | 45 | 1, 3, 4, 6 |
| Lung (LN-300) | | 50 | 2, 5, 6 |
| Lung (LN-450) | | 51 | 1, 2, 5, 6 |
| Blood (40) | | 96 | 6, 7 |
| Blood (70) | | 97 | 1, 6, 7 |
| Blood (100) | | 98 | 2, 6, 7 |
| Blood 40 + 2 mg/mL Iodine | | 110 | 2, 3, 4, 6, 7 |
| Blood 40 + 4 mg/mL Iodine | | 111 | 1, 2, 3, 4, 6, 7 |
| Inner bone | | 144 | 5, 8 |
| Bone (B200) | | 145 | 1, 5, 8 |
| Bone (CB2-30%) | | 146 | 2, 5, 8 |
| Bone (CB2-50%) | | | |
| Cortical Bone (SB3) | | 147 | 1, 2, 5, 8 |
| Calcium 50 mg/mL | | 164 | 3, 6, 8 |
| Calcium 100 mg/mL | | 165 | 1, 3, 6, 8 |
| Calcium 200 mg/mL | | 166 | 2, 3, 6, 8 |
| Calcium 300 mg/mL | | 167 | 1, 2, 3, 6, 8 |
| Calcium 400 mg/mL | | 168 | 4, 6, 8 |
| Calcium 500 mg/mL | | 169 | 1, 4, 6, 8 |
| Calcium 600 mg/mL | | 170 | 2, 4, 6, 8 |
| Iodine 2 mg/mL | | 192 | 7, 8 |
| Iodine 2.5 mg/mL | | 193 | 1, 7, 8 |
| Iodine 5 mg/mL | | 194 | 2, 7, 8 |
| Iodine 7.5 mg/mL | | 195 | 1, 2, 7, 8 |
| Iodine 10 mg/mL | | 196 | 3, 7, 8 |
| Iodine 15 mg/mL | | 197 | 1, 3, 7, 8 |
| Iodine 20 mg/mL | | 198 | 2, 3, 7, 8 |
| Iodine concentrations in HE | | 201-207 | |
| Iodine 5 mg/mL at 2 mm diam | | 210 | 2, 5, 7, 8 |
| Iodine 5 mg/mL at 5 mm diam | | 211 | 1, 2, 5, 7, 8 |
| Iodine 5 mg/mL at 10 mm diam | | 212 | 3, 5, 7, 8 |
| Iodine concentrations in HE, narrow diam | | 215-217 | |
| Aluminum | | 240 | 5, 6, 7, 8 |
| Titanium | | 241 | 1, 5, 6, 7, 8 |
| Stainless steel | | 242 | 2, 5, 6, 7, 8 |

Figure 4C:
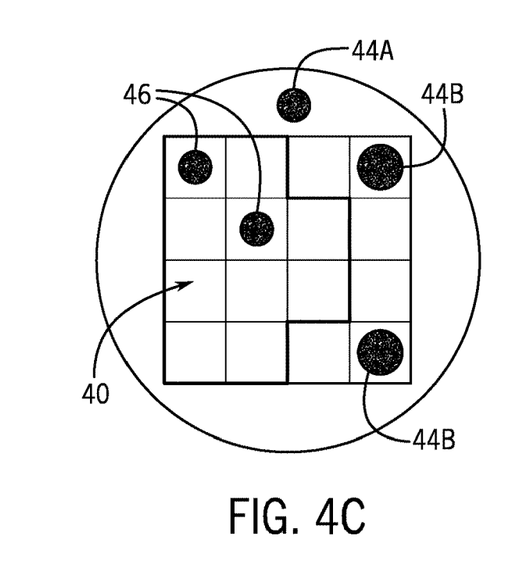
Figure 4D:
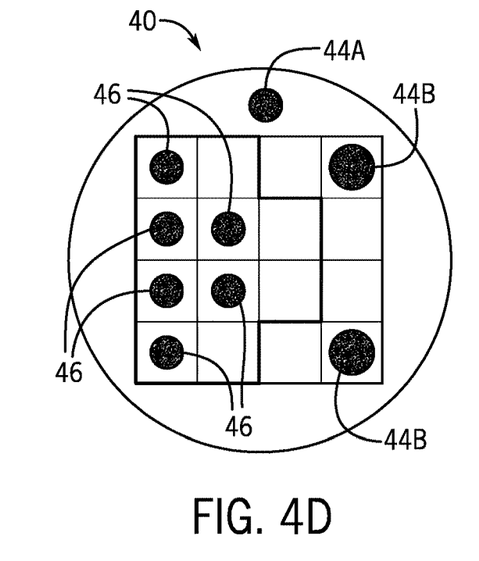
Figure 4E:
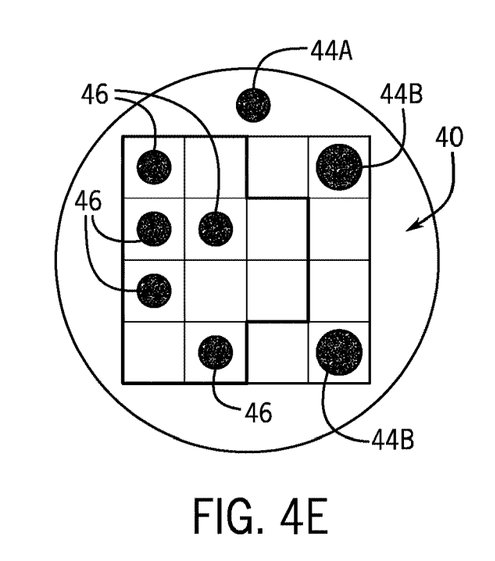

FIGS. 4C-4E depict still further exemplary embodiments of rod identifiers 40 as may be used. These figures also provide a textual indication of rods for which these rod identifiers exemplarily represent. In addition to providing exemplary arrangements of the rod identifiers 40, FIGS. 4C-4E provide examples of phantoms or rods which may be used. The rod identifier 40 of FIG. 4C exemplarily identifies a tissue mimicking material for example brain HE material. According to Table 1 above, Brain HE material is exemplarily encoded by the number 33 which is represented by "activation" of the unit markers 46 at bit locations #1 and #6. The rod identifier 40 of FIG. 4D exemplarily represents a material representative of a combination of an anatomic phantom (e.g. blood) combined with an additional material (e.g. 4 mg/mL iodine). According to Table 1 above, the Blood 40+4 mg/mL Iodine phantom material is exemplarily encoded by the number 111 which is represented by "activation" of the unit markers 46 at bit locations #1, #2, #3, #4, #6, and #7. The rod identifier 40 of FIG. 4E exemplarily represents a rod of material marking a particular concentration of calcium (e.g. 300 mg/mL). According to Table 1 above, the calcium 300 mg/mL phantom material is exemplarily encoded by the number 167 which is represented by "activation" of the unit markers 46 at bit locations #1, #2, #3, #6, and #8. These are exemplary and nonlimiting embodiments of the types of material rod that may be represented in the rod identifiers 40.

While the reference markers 44 are exemplarily depicted as being distinct from the unit markers 46, it will be recognized that there are other embodiments where these need not be physically distinct markers. For example, some codes might be sufficiently simple that the patterns are unambiguous with regards to size, orientation, and inversion, meaning that explicit reference markers might not be required. In one such embodiment, the encoded identification could be indicated by counting a number of markers in the rod. In another embodiment, the markers could be placed at different radii from the center and/or with different marker diameters. In a further embodiment, a number, size, and/or shape of each of the markers in combination encodes the identifier. In yet another embodiment, the markers may be constrained to sizes or constellations of markers that provide an identification that is unique regardless of rotation, scale, and/or inversion.

In other embodiments, two or more different properties of the markers may be used to provide the function of both the unit markers and the reference markers. These properties may be size, shape, density, electron density, magnetic moment, elemental composition, attenuation, mass, number and/or positional relationship of markers, and others as may be recognized by a person of ordinary skill in the art. With two or more detectable properties related to each marker, these may be used to encode identifiers in manners that are independent of rotation, inversion, or scale, as each marker can encode multiple values with the combination of properties. As such, certain rod markers, such as some of the unit markers 46, could be created with a distinctive characteristic such that they served as both reference and unit markers. In one example, the positions of the reference markers as described above may be used, while one or more of e.g. a size, shape, and/or electron density of the markers encodes the identifier.

Figure 5:
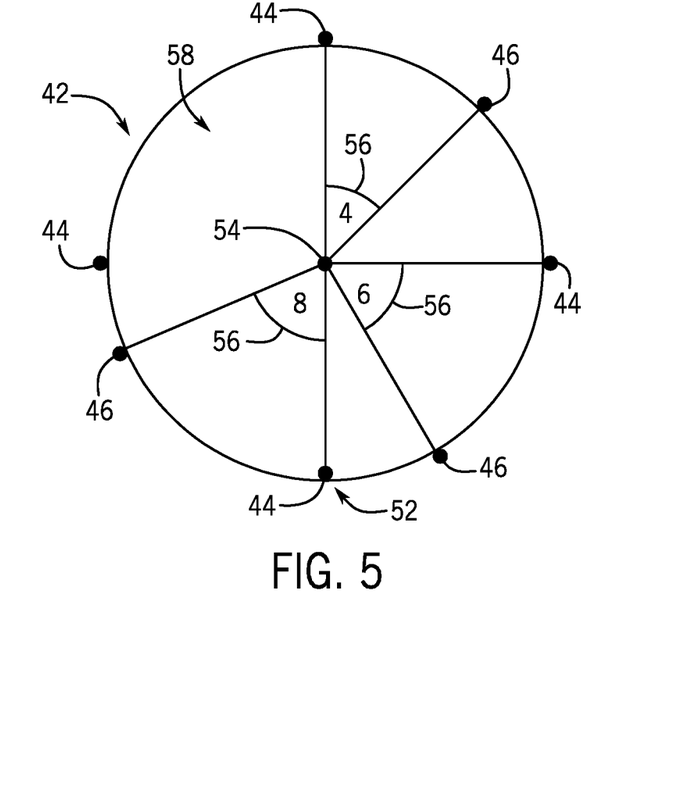
FIG. 5 depicts an additional exemplary embodiment of a phantom identifier.

FIG. 5 depicts an additional exemplary embodiment of a phantom identifier 42. It will be recognized from the present disclosure that exemplary embodiments of identifiers as presented herein, including FIGS. 4A-4E, are characterized as rod identifiers and that the further identifiers as described herein, including the phantom identifiers 42 depicted in FIG. 5 are characterized as phantom identifiers 42. Despite these two characterizations, it will be recognized that in embodiments either or both types of disclosed identifiers may be used. In embodiments, either arrangement of identifier may be used interchangeably for identification unitary phantoms, phantom bases, and/or phantom components. It will be recognized that in embodiments, multiple examples of the identifiers as disclosed herein may be used within a single phantom or phantom system. Furthermore, depending upon the arrangement, function and use of a particular phantom, phantom dose, or phantom component, one of the embodiments of identifiers as disclosed herein may be selected and used. As a non-limiting embodiment, a phantom identifier 42 as described herein with respect to FIG. 5 may be used to identify a particular phantom base while phantom identifiers 40 as previously described above with may be used to identify individual rods 36 inserted into the phantom base 32.

It is already known in the art to include one or more reference markers 44 into a phantom or phantom base. The reference markers 44 are exemplarily metal BBs that are positioned in the edge of the phantom or phantom base and represent the cardinal angles of the phantom or phantom base. These are used in the acquisition procedure in order to properly align the phantom with the imaging or therapeutic system. These standard alignment reference markers may further be used to reference or generally align an acquired image of the phantom.

In an embodiment of the identifiers 42 as disclosed herein, the phantom identifier 42 includes a differentiation marker 52, which is exemplarily in the position of one of the reference markers 44 although modified in a manner so as to distinguish it from the other alignment reference markers 46. For example, the differentiation marker 52 may exemplarily be of a different size or shape or other detectable property (e.g. density or mass) such that it still functions to provide an alignment reference, but also differentiates, such as either a top or a bottom of the phantom or phantom base, or phantom module. This helps to provide a further reference as to the orientation of the phantom as acquired during the calibration or quality assurance procedure. In this manner, the differentiation marker 52 may serve as similar function as the reference marker 44A described in the embodiments above, and used to determine image rotation.

In addition to the reference markers 44, including the differentiating marker 52, the phantom identifier 42 includes additional unit markers 46 that are exemplarily positioned absent the object perimeter between respective reference markers 44. In an exemplary embodiment, there is a unit marker 46 located in three of the four quadrants defined by the reference markers 44. By providing unit markers in three of the four quadrants and leaving the fourth quadrant blank, the quadrant without a unit marker can be identified and used to identify image inversion. In an embodiment a relationship between the differentiation marker 52 and the blank quadrant can be evaluated to ensure that the image is properly oriented.

Each of the quadrants with unit markers may exemplarily be incremented in a series of increments from a center point of the object with each increment representing a decimal place number when the quadrants are read either in a clockwise or counterclockwise direction. In one exemplary embodiment each arc increment is a nine degree increment. Each of the nine degree increments can therefore represent an integer value between 1 and 9. In another embodiment, a lack of a reference marker in a quadrant in which one is expected can be used to indicate the "0" value. In another embodiment, the increments may be made smaller so as to accommodate a greater number of integer values in a quadrant. In a still further embodiment, the unit markers 46 may be positioned radically interior or exterior of the reference markers 44 so that a unit marker 46 may be located at a same position as a reference marker 44.

By way of the reference markers 44 a center point 54 can be determined and representative angles 56 exemplarily between a reference marker 44 and an adjacent unit marker 46 can be identified to determine each of the three integer values. In the exemplary embodiment depicted in FIG. 5, for example, the angles of the unit markers 46 when taken clockwise from the open or blank quadrant 58 are exemplarily 36 degrees, 54 degrees, and 72 degrees. These angles exemplarily represent the numbers 4, 6, and 8 or exemplarily the code 468, which may then be identified by way of reference to the lookup table. In another example, the angles 18 degrees, 36 degrees, 9 degrees may be identified from the unit markers when taken clockwise from the blank quadrant. This combination exemplarily encodes the number 241 which according to the Table 1 above indicates titanium material. Using phantom identifier 42 as described above, exemplarily one thousand different codes (000-999) could be represented.

Figure 6:
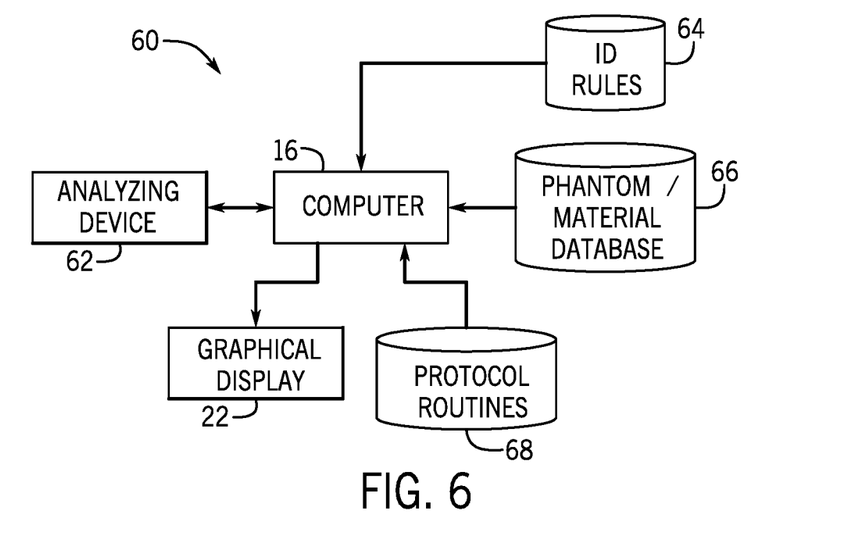
FIG. 6 is a system diagram of an exemplary embodiment of a protocol system.

FIG. 6 depicts an exemplary embodiment of a protocol system 60. The protocol system 60 as discussed above, exemplarily performs any of a number of calibration and/or quality assurance protocols within an imaging system or radiotherapy system. In an exemplary embodiment, the protocol system 60 may be implemented using the imaging system 10. It will be recognized that reference numerals may be used herein to reference similar components between the imaging system 10 and the protocol system 60.

The protocol system 60 includes an analyzing device 62. The analyzing device 62, as discussed above, may exemplarily be an imaging device, for example a CT device or radiotherapeutic device. The analyzing device 62 is communicatively connected to a computer 16. The analyzing device 62 performs an acquisition of data from a phantom (not depicted) as described in the embodiments above. The analysis by the analyzing device may exemplarily be an image, a scan or another type of acquisition of information from the phantom. This information is provided to the computer 16. The computer analyzes the acquired information, exemplarily a CT image exemplarily referencing a scan plane of the acquired image data that coincides with one or more identifiers associated with the phantom. In an exemplary embodiment of a phantom comprised of a phantom base and a plurality of independently arranged rods, the computer 16 references a scan plane known to include the rod identifiers and/or phantom identifiers.

In an exemplary embodiment, the computer applies identification rules 64 to the image of the identified scan plane. In an exemplary embodiment, the identification rules 64 are embodied in computer readable code stored on a computer readable medium and accessible and executable by the computer 16. For example, the computer 16 carries out the actions as described in further detail herein with respect to the method 100 depicted in FIG. 7. After applying the identification rules 64 to the at least one image, the computer identifies the numbers encoded in the detected identifiers and uses these numbers to reference a phantom and material database 66. The phantom and material database 66 for example may include the data of Table 1 above. With the phantom, phantom base, and/or phantom rod identified, the computer 16 can apply one or more protocol routines available from a computer readable medium 68 in communication with the computer 16. In an exemplary embodiment, depending upon the identified phantom, phantom base, or phantom rods, the computer 16 may automatedly select one or more protocol routines. The results of the protocol routines may be presented on the graphical display 22 or, in the case of calibration routines may exemplarily be used to modify aspects of the analyzing device 62 and/or computer 16 used in further diagnostic or therapeutic operations by the analyzing device 62.

In an exemplary or non-limiting embodiment the computer may identify the inclusion of one or more multiple energy (ME) or dual energy (DE) rods. These rods may exemplarily include complex material, for example materials that represent particular concentrations of calcium and/or iodine in blood or may represent a physical structure and/or material properties of a blood vessel or specific blood vessel condition (e.g. aneurysms) within a particular type of body tissue (e.g. brain tissue or cardiac tissue). Upon identification of one or more of these exemplary specialized rods, the computer 16 may access and apply testing protocols or analysis routines that pertain to or use the information from scans of these more complex phantoms.

Figure 7:
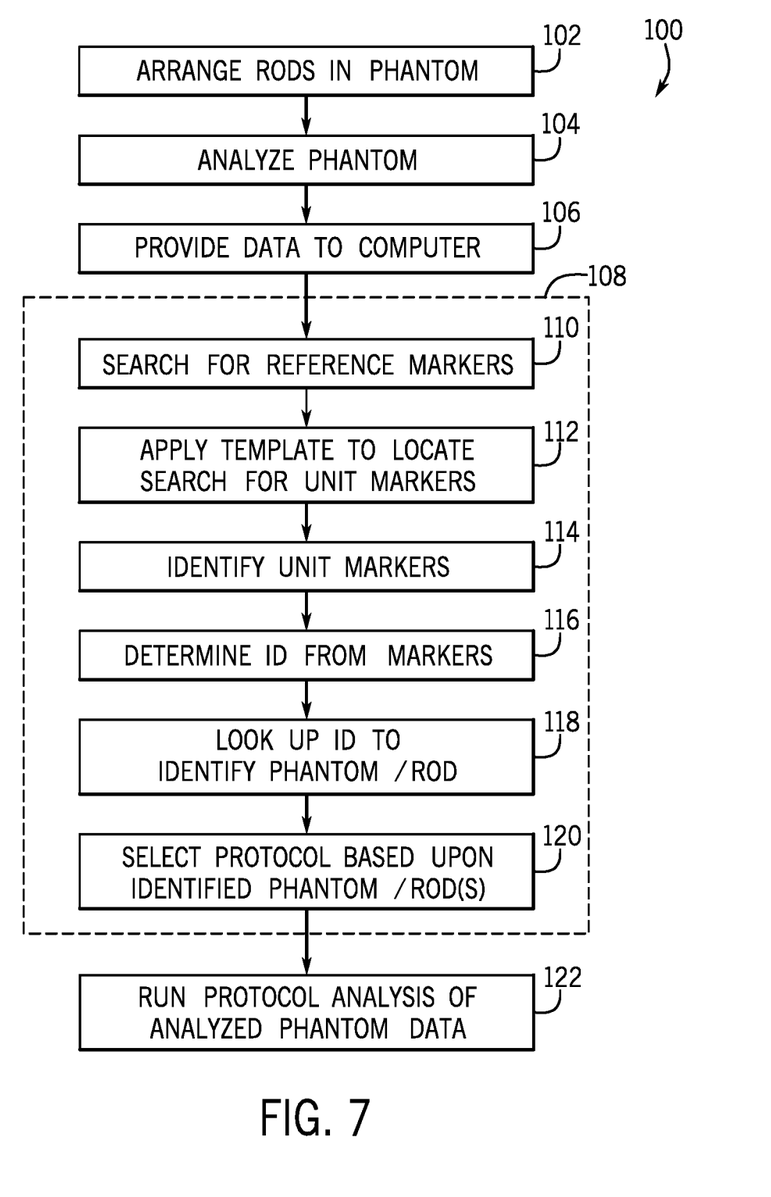
FIG. 7 is a flow chart that depicts an exemplary embodiment of a method of processing a phantom.

As referenced above, FIG. 7 is a flow chart that depicts an exemplary embodiment of a method 100 of processing a phantom. The method 100 begins at 102 wherein the phantom components, exemplarily insert rods are arranged within a phantom. In an exemplary embodiment, the rods may be interchangeably inserted into a phantom base, while in other embodiments, the phantom components may be formed as an integral part of the phantom or as modular sections of a phantom. Next, at 104, the phantom is analyzed with the device to be evaluated. In exemplary embodiments, the device is a medical imaging device or a radiotherapy device, and in the exemplary embodiment used herein for description purposes, the device is a CT imaging device. In such exemplary embodiments, the phantom is analyzed at 104 by acquiring CT images of the phantom. The CT projection images and imaging data is provided to the computer at 106. In an exemplary embodiment, the CT images are exemplarily reconstructed as slice images along a plurality of scan planes through the phantom. These slice images may be provided to the computer from the CT imaging device, or may be reconstructed by the computer itself.

The portion of the method as denoted by reference number 108 exemplarily may be used to identify a phantom as a whole, a phantom base, and/or one or more phantom components, which may exemplarily be a plurality of sample rods inserted into a phantom base. It will be recognized that the features as denoted by 108 may be applied sequentially or in parallel to identify more than one phantom, phantom base and/or phantom components. It will be further recognized that in an exemplary embodiment the features set out at 108 may be carried out first to identify the phantom or phantom base, as in the case of a unitary phantom, identification of the phantom may further already provide the information regarding the locations of phantom components and identification whereas identification of a particular phantom base may further facilitate the identification of the phantom components inserted in the phantom base by informing a number and location of phantom components to be identified. The features set out at 108 may then be repeated further using the information of the phantom base to identify each of the phantom components inserted and held in the phantom base.

The method 100 and sub-method 108 includes identifying unit markers at 114. It will be recognized that any of the unit markers as described in the present application may be used in embodiments of the method 100. Persons of ordinary skill in the art will recognize further exemplary embodiments of unit markers that encode the identification of the phantom, phantom base, or individual phantom components. As previously noted, the identification of the unit markers may include identification of one or more properties of the unit markers identifiable in the acquired image, the identity and property values contribute to encode the identification. These properties, may include, but are not limited to, the density, electron density, magnetic moment, shape, dimensions, elemental composition, attenuation, mass, position, and relative position between unit markers. In the example of the rod identifiers, the unit markers are located at representative bit locations associated with a predefined grid. In another example the unit encode a value represented by an angle between each unit marker and an exemplary reference marker. It will be recognized that in embodiments, the unit markers are identified at 114 by using image processing techniques applied to the obtained images of the phantom, phantom base, and/or phantom components. Such image processing techniques are known to persons of ordinary skill in the art to be able to identify the encoding properties of the unit markers from the obtained images.

As noted above, some forms of unit markers may be orientation specific and therefore, some embodiments of the method 100 include the further feature of searching for reference marker at 110. As indicated in the method 100, this feature may exemplarily take place prior to identifying unit markers at 114 as this may facilitate unit marker identification. The search for reference markers at 110 exemplarily includes starting at a center of a location where the rod is to be expected in the case of a rod identification or starting at the center of the phantom in a phantom identification. From that starting point, the method searches for the reference markers, for example by rastering a space about the identified center, to identify the reference markers. In the embodiment of the rod identification, the system may look for the two reference markers within the grid, exemplarily a 4×4 grid, to find the space with the lowest sum. In an alternative embodiment, a template of the reference marker may be applied to the image to find the best template match with the reference marker locations. In exemplary embodiments, as reference markers are found, those reference markers can be used to simplify and refine the search for the remaining reference markers. For example, in disclosed embodiments of the two large reference markers are identified, the alignment marker should be in one of four locations based upon rotation and inversion of the rod and the image.

In a still further exemplarily embodiment, the reference markers of identified and as explained above used to evaluate the rotation, inversion, and scale of the acquired images. From these determinations, the appropriate transformative operations for the images can be determined and applied as needed to the acquired images before the identifier is detected and interpreted.

Once the reference markers are found, a template can be applied at 112 to locate the search for the unit markers. In the example of the rod identifier, the template may be the 4×4 grid within which two of the reference markers are located while in the phantom identifier disclosed above. The search for the unit markers will be refined to the areas between reference markers along a unit circle connecting the reference markers.

Returning to the method 100, an identification code is determined from the identified unit markers at 116. In the example of the rod identifier, the identification code is a sum of the "on" bits represented by the identified unit markers. In the exemplary phantom identifier the ID code uses the hundreds, tens, and ones decimal values represented by each of the identified unit markers.

At 118 the determined identification code is used with a table to look up the identification of the phantom, phantom base, phantom module, or rod. The identification of the phantom, phantom base, phantom module, or rod provides the known characteristics or associated values of the identified product as may be used or relied upon in various calibration and/or quality assurance protocols.

Next, at 120, in an optional step, one or more protocols may be automatedly selected based upon the identified phantom and/or rods. As noted above, specialized phantoms and/or specialized rod or rod locations within a phantom base may be associated with or specific to particular calibration or quality assurance protocols and therefore upon a detection of one or more of these arrangements or devices, embodiments may automatically select protocols to be used with a analysis of the identified phantom. At 122 the protocol analysis of the analyzed phantom is performed. In an exemplary embodiment, a calibration of electron density may compare the measured CT device/Hounsfield Units provided from the analysis of the phantom at 104 to the actual electron density values of the rods as known from identifying the rod and looking them up in a table to identify them. The measured and real values may be used to create a calibration curve used in future imaging and radiotherapy procedures by the CT device.

Citations to a number of references are made herein. The cited references are incorporated by reference herein in their entireties. In the event that there is an inconsistency between a definition of a term in the specification as compared to a definition of the term in a cited reference, the term should be interpreted based on the definition in the specification.

In the above description, certain terms have been used for brevity, clarity, and understanding. No unnecessary limitations are to be inferred therefrom beyond the requirement of the prior art because such terms are used for descriptive purposes and are intended to be broadly construed. The different systems and method steps described herein may be used alone or in combination with other systems and methods. It is to be expected that various equivalents, alternatives and modifications are possible within the scope of the appended claims.

The functional block diagrams, operational sequences, and flow diagrams provided in the Figures are representative of exemplary architectures, environments, and methodologies for performing novel aspects of the disclosure. While, for purposes of simplicity of explanation, the methodologies included herein may be in the form of a functional diagram, operational sequence, or flow diagram, and may be described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology can alternatively be represented as a series of interrelated states or events, such as in a state diagram. Moreover, not all acts illustrated in a methodology may be required for a novel implementation.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A phantom system for use in calibration of a medical device, the phantom system comprising:
   a phantom base comprising at least a first material;
   a first phantom component positioned relative the phantom base, the first phantom component comprising a second material;
   a first phantom component identifier connected to the first phantom component, the first phantom component identifier comprising at least one first phantom component unit marker, wherein the at least one first phantom component unit marker encodes an identification of the second material;
   a second phantom component positioned relative the phantom base, the second phantom component comprising a third material; and
   a second phantom component identifier connected to the second phantom component, the second phantom component identifier comprising at least one second phantom component unit marker, wherein the at least one second phantom component unit marker encodes an identification of the third material.

2. The system of claim 1, wherein the second material is different from the first material and the third material is different from the first material and the second material.

3. The system of claim 1, wherein the first phantom component and the second phantom component are removably received within the phantom base.

4. The system of claim 1, wherein a first scan plane extends through the first phantom component, the second phantom component, and the phantom base and a second scan plane extends through portions of the first phantom component and the second phantom component that extend exterior of the phantom base.

5. The phantom system of claim 1 wherein the first phantom component identifier comprises a plurality of holes in the second material of the first phantom component and the second phantom component identifier comprises a plurality of holes in the third material of the second phantom component.

6. The phantom system of claim 1, wherein the at least one first phantom component unit marker comprises a plurality of unit markers that provide a binary encoding of the second material and the at least one second phantom component unit marker comprises a plurality of unit markers that provide a binary encoding of the third material.

7. The phantom system of claim 1, wherein the first phantom component identifier is internal to the first phantom component and the second phantom component identifier is internal to the second phantom component.

8. The phantom system of claim 1, wherein the first phantom component identifier comprises at least one first phantom component reference marker indicative of an orientation of the first phantom component identifier and wherein the second phantom component identifier comprises at least one second phantom component reference marker indicative of an orientation of the second phantom component identifier.

9. The phantom system of claim 1, further comprising a plurality of phantom base reference markers and a plurality of phantom base unit markers arranged within the phantom base, wherein the plurality of phantom base reference markers are indicative of an orientation of the phantom base and the plurality of phantom base unit markers encode an identification of the phantom base.

10. The phantom system of claim 1 wherein the medical device is a radiographic device or a radiotherapeutic device.

11. The phantom system of claim 1 wherein the first material is different form the second material and the third material in one or more of: density, electron density, magnetic moment, elemental composition, attenuation, and mass.

12. The phantom system of claim 1, further comprising:
   a first label secured to an end of the first phantom component, wherein the first phantom component identifier is internal to the first phantom component behind the first label; and a second label secured to an end of the second phantom component wherein the second phantom component identifier is internal to the second phantom component behind the second label.

13. The phantom system of claim 1 wherein the at least one reference marker is physically larger than the at least one unit marker.

14. The phantom system of claim 1, wherein the at least one first phantom component unit marker encodes the second material in a first binary code having at least six bits, and the at least one second phantom component unit marker encodes the third material in a second binary code having at least six bits.

15. The phantom system of claim 1, wherein:
  the first phantom component comprises a first end cap which comprises the at least one first phantom component unit marker; and
  the second phantom component comprises a second end cap which comprises the at least one second phantom component unit marker.

16. The phantom system of claim 1, wherein:
  a first scan plan extends through the first phantom component and the second phantom component, and extends through the at least one first phantom component unit marker and the at least one second phantom component unit marker; and
  a second scan plane extends through the first phantom component, the second phantom component and the phantom base at a position free of the at least one first phantom component unit marker and the at least one second phantom component unit marker.

17. The phantom system of claim 1, wherein the first phantom component comprises an anatomical phantom comprising a fourth material within the second material, wherein the at least one first phantom component unit marker encodes an identification of the anatomical phantom, the second material, and the fourth material.

* * * * *